US00PP27083P3

(12) United States Plant Patent
Lee

(10) Patent No.: US PP27,083 P3
(45) Date of Patent: Aug. 23, 2016

(54) ***RHODODENDRON* PLANT NAMED 'QBACKB'**

(50) Latin Name: ***Rhododendron* hybrid**
Varietal Denomination: QBACKB

(71) Applicant: Robert Edward Lee, Independence, LA (US)

(72) Inventor: Robert Edward Lee, Independence, LA (US)

(73) Assignee: Plant Development Services Inc., Loxley, AL (US)

( * ) Notice: Subject to any disclaimer, the term of this patent is extended or adjusted under 35 U.S.C. 154(b) by 146 days.

(21) Appl. No.: 14/120,167

(22) Filed: May 1, 2014

(65) Prior Publication Data

US 2015/0319899 P1 Nov. 5, 2015

(51) Int. Cl.
*A01H 5/02* (2006.01)

(52) U.S. Cl.
USPC ..... Plt./238

(58) Field of Classification Search
USPC ..... Plt./238
See application file for complete search history.

*Primary Examiner* — Keith Robinson
(74) *Attorney, Agent, or Firm* — Cassandra Bright

(57) ABSTRACT

A new and distinct *Rhododendron* cultivar named 'QBackB' is disclosed, characterized by distinctive large, fragrant, yellow-orange flowers with orange-red flushing. Plants are deciduous, tolerant of heat and humidity, tolerant of mildew and begin blooming before foliage emerges. The new cultivar is a *Rhododendron*, suitable for ornamental garden purposes.

2 Drawing Sheets

Figure 1:
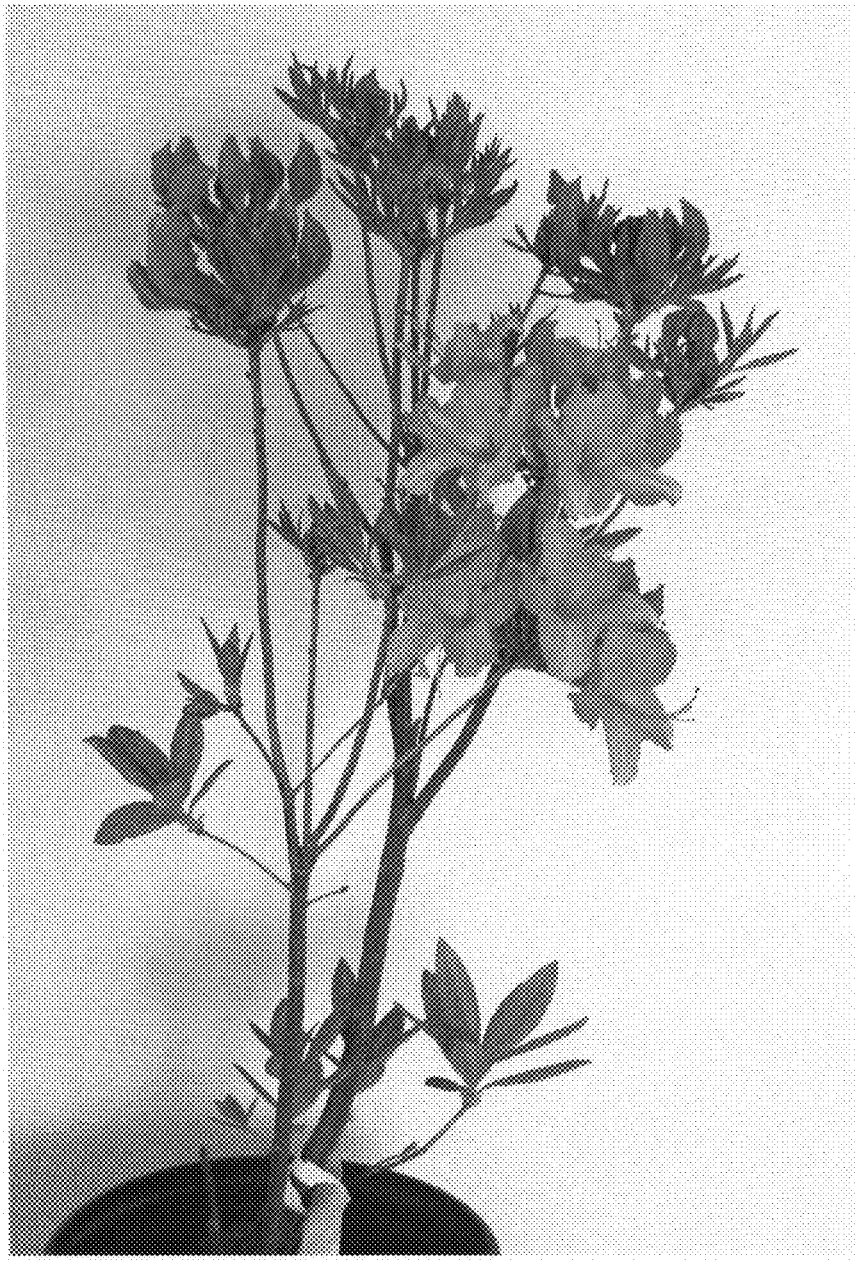

Latin name of the genus and species: *Rhododendron* hybrid.

Variety denomination: 'QBackB'.

BACKGROUND OF THE INVENTION

The new cultivar is a product of a planned breeding program by the inventor, Robert Edward Lee. The inventor's intention was to develop *Rhododendron* hybrid plants with tolerance for heat and humidity and fragrant flowers with vibrant colors. This new variety, hereinafter referred to as 'QBACKB', was discovered as a seedling, resulting from the crossing of an unnamed, unpatented proprietary seedling, resulting from the open pollination of *Rhododendron austrinum* with *Rhododendron* hybrid 'Gibraltar' with the pollen parent, *Rhododendron* hybrid 'Chectco', unpatented. The cross was performed during the Spring of 1984, and the new variety selected by the inventor during Spring of 1990 in Folsom, La.

After identifying the new variety as a potentially interesting selection, the inventor first propagated 'QBACKB' by vegetative softwood cuttings during late Spring of 1990 at a commercial nursery in Folsom, La. The inventor continued confidential and controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'QBACKB' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'QBACKB' These characteristics in combination distinguish 'QBACKB' as a new and distinct *Rhododendron* cultivar:

1. Vibrant yellow-orange flowers flushed with red-orange.
2. Plant naturally forms a small tree to a large bush form, with maturity 4 to 6 feet wide and 6 to 8 feet tall, and tolerates pruning to a smaller size.
3. Fragrant flowers
4. Manageable growth habit
5. Large bloom size
6. Large bloom truss
7. Blooms open before foliage appears in established landscape planning
8. Heat and humidity tolerant
9. Increased tolerance to *Erysiphe azaleae*

COMPARISON TO PARENT VARIETY

'QBACKB' is similar in most horticultural characteristics to the unnamed seed parent variety. Plants of the new cultivar 'QBACKB' however, produce larger flowers, and begin blooming later than the seed parent. Additionally, plant habit is overall more manageable and better suited to landscape situation than the seed parent.

'QBACKB' is similar in most horticultural characteristics to the pollen parent *Rhododendron* hybrid 'Chectco'. Plants of the new cultivar 'QBACKB' however, differ in the following characteristics:

1. More heat tolerant than pollen parent.
2. Slightly smaller flower size than pollen parent.
3. More mildew resistance than pollen parent.
4. Earlier blooming time than pollen parent.
5. More manageable and attractive growth habit than the pollen parent.

COMMERCIAL COMPARISON

'QBACKB' can be compared to the commercial variety *Rhododendron* hybrid 'Admiral Semmes' unpatented. Plants of the new cultivar 'QBACKB' are similar to plants of 'Admiral Semmes' in most horticultural characteristics, however, plants of the new cultivar 'QBACKB' differ in the following characteristics:

1. More vibrant flower color of the new variety, with flushes of red and orange-red.
2. The new variety begins blooming earlier than 'Admiral Semmes'(.)
3. 'QBACKB' reaches a mature height of 6 to 8 feet, 'Admiral Semmes' reaches a mature height of approximately 4 to 5 feet.

'QBACKB' can be compared to the commercial variety *Rhododendron* hybrid 'QBackA', Plant patent application Ser. No. 14/120,168. Plants of the new cultivar 'QBACKB' are similar to plants of 'QBackA' in most horticultural characteristics, however, plants of the new cultivar 'QBACKB' differ in the following characteristics:

1. 'QBACKB' has yellow-orange flowers with orange-red flush, whereas 'QBackA' has orange flowers, streaked with orange-red.
2. 'QBACKB' begins blooming approximately 2 weeks later than 'QBackA'.
3. 'QBACKB' reaches a mature height of 6 to 8 feet, 'QBackA' reaches a mature height of approximately 8 to 10 feet.

BRIEF DESCRIPTION OF THE PHOTOGRAPHS

The accompanying photograph in FIG. 1 illustrates in full color a typical plant of 'QBACKB', of approximately 2 years old.

Figure 2:
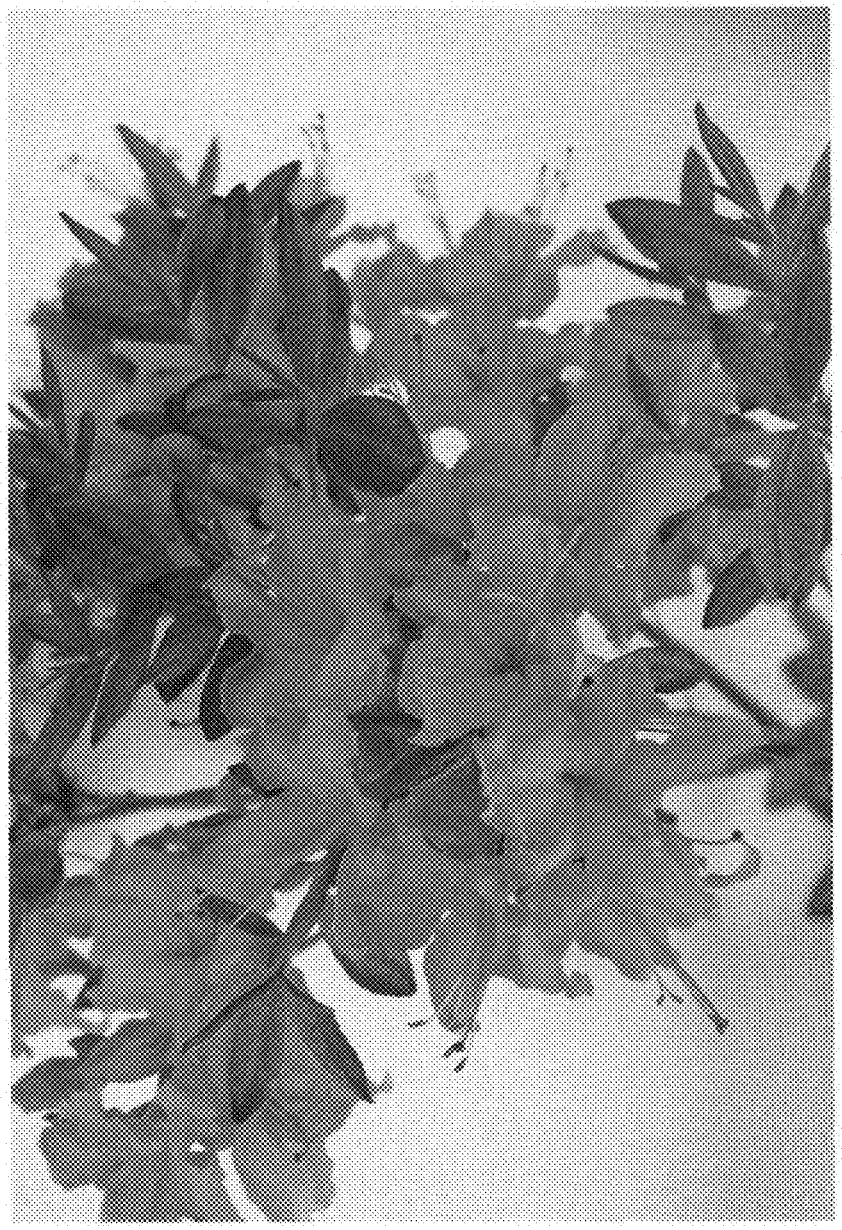

FIG. 2 illustrates a close up of typical flowers of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'QBACKB' plants grown outdoors in Loxley, Ala. Plants are approximately 2 years old, in a 2 gallon nursery container. Measurements and numerical values represent averages of typical plant types.

Botanical classification: *Rhododendron* hybrid 'QBACKB'.

PROPAGATION

Typically by semi-hardwood cuttings in Spring and Summer.

Root description: Fine, fibrous young roots, well branched. Colored near RHS Grey-Brown N199A.

Time (approximate days) to initiate roots: 30 to 60 days at 70 to 80 degrees F. day temperatures and 55 to 65 degrees F. night temperatures.

Time (approximate days) to produce a rooted plant: Approximately 150-210 days at 70 to 80 degrees F. day temperatures and 55 to 65 degrees F. night temperatures.

PLANT

Growth habit: Upright, deciduous woody shrub.

Height: Approximately 45 cm to top of foliar and flowering plane.

Plant spread: Approximately 22 cm.

Branching characteristics: Average 4 to 10 primary branches from the center of the plant, after giving a low pinch, near soil line. Branches occur at approximately 15° to 25° angles. Each primary branch has an average of 2 to 4 lateral branches.

Primary branches:

*Length of primary branches*.—Average 8 cm to 20 cm, then splits into lateral branches.

*Diameter of primary branches*.—Approximately 0.7 cm.

*Primary branch strength*.—Very strong, difficult to break.

*Primary branch color*.—Near RHS Grey-Brown 199B.

*Primary branch texture*.—Young growth pubescent to nearly hirsute. Hairs, approximately 0.15 cm long, colored near Yellow-Green 145B. Older growth moderately scaly and hirsute.

*Lateral branches*.—Number of Lateral Branches: Average 2 to 4 per primary branch. Length of Lateral Branches: Average 4 cm to 8 cm, then splits into more branches. Diameter of Lateral Branches: Average 0.4 cm. Lateral Branch Strength: Very strong, not flexible, difficult to break. Lateral Branch Color: Near RHS Grey-Brown N199B. Lateral Branch texture: Scaly, hirsute.

*Internode length*.—Average 5 cm.

*Age of plant described*.—Approximately 2 years.

FOLIAGE

Leaf:

*Type*.—Simple.

*Arrangement*.—Leaves occur in a whorl at the end of branches. Foliage emerges after flowering begins.

*Average length*.—Approximately 5.9 cm.

*Average width*.—Approximately 2.4 cm.

*Shape of blade*.—Elliptic.

*Apex*.—Acute to slightly mucronate.

*Base*.—Attenuate.

*Attachment*.—Sessile.

*Margin*.—Entire.

*Texture of top surface*.—Pubescent. Hairs appressed.

*Texture of bottom surface*.—Faintly pubescent. More hairs present along main vein and margin.

*Appearance of top surface*.—Matte, not glossy.

*Appearance of bottom surface*.—Matte, not glossy.

*Color*.—Young foliage upper side: Near RHS Yellow-Green 144A. Mucronate apex near Greyed-Purple 183A. Faint flush on apex near Greyed-Purple 183A. Young foliage under side: Near RHS Yellow-Green 144B. Mature foliage upper side: Near RHS Yellow-Green 144A, faintly flushed Greyed-Orange 175A. Mature foliage under side: Near RHS Green 138B.

*Venation*.—Type: Pinnate. Underside of leaf veins prominently raised. Venation color upper side: Near RHS Yellow-Green 153D. Venation color under side: Near RHS Yellow-Green 153B.

FLOWER

Bloom period: Plants flower in the Spring, around late April, with a 2 to 3 week flowering period. Flowering again during the same year has not been observed.

Flower:

*Arrangement*.—Axillary clusters of single, perfect, open funnel shaped individual flowers. Typically 5 open flowers and 5 buds per cluster.

Inflorescence:

*Height*.—Average 9.0 cm.

*Diameter*.—Average 15.0 cm.

*Overall shape*.—Globular.

Peduncle: No true peduncle, flower cluster emerges directly from lateral woody stem.

Pedicel:

*Length*.—Average 1.3 cm.

*Diameter*.—0.25 cm.

*Color*.—Near RHS Yellow-Green 144B, slightly flushed with Greyed-Red 180A near flower attachment.

*Texture*.—Densely pubescent.

*Aspect*.—Straight. Angle of attachment, approximately 75° angle from stem, outermost flowers.

*Strength*.—Strong and flexible.

Flowers:

*Length*.—Average 5.4 cm.

*Diameter*.—Average 7.2 cm.

*Facing direction*.—Outwardly and upwardly facing.

*Persistent or self-cleaning*.—Petals self-cleaning.

*Fragrance*.—Very strong sweet fragrance.

*Tube*.—Tube length: Approximately 2.4 cm. Tube width a widest point: Approximately 1.1 cm. Tube width and narrowest point: Approximately 0.6 cm.

*Color*.—Inner surface at first opening: Near RHS Yellow-Orange 14C. Outer surface at first opening: Near RHS Yellow-Orange 14C, and heavily flushed Yellow-Orange 14A. Inner surface at maturity: Near RHS Yellow-Orange 14C. Flushed Orange-Red 34C. Outer surface at maturity: Near RHS Yellow-Orange 14C. Small streaks of Orange-Red 34A. Inner surface at fading: Near RHS Yellow-Orange 14D. Outer surface at fading: Near RHS Yellow-Orange 18A. Large streaks of Orange-Red 34A.

*Petals*.—Unfused petal segments: Length: Approximately 3.4 cm. Width: Approximately 2.07 cm. Apex: Ruffled. Shape of petal: Unfused portion, obovate. Petal margin: Ruffled. Petal Arrangement: Approximately ⅓ fused from base. Unfused section overlapping. Petal Number: 5. Petal Texture: Smooth, all surfaces.

*Color*.—Inner surface at first opening: Near RHS Yellow-Orange 14C. Flushed Orange-Red 34C. Outer surface at first opening: Near RHS Yellow-Orange 14D. Flushed Orange-Red 34C. Inner surface at maturity: Near RHS Yellow-Orange 14C. Flushed Orange-Red N34C. Outer surface at maturity: Near RHS Yellow-Orange 15D. Flushed Red 39A. Inner surface at fading: Near RHS Yellow-Orange 14D. Flushed Red 39A. Outer surface at fading: Near RHS Yellow-Orange 14D. Flushed Red 39A.

Bud:

*Shape*.—Elliptic, with inflated apical end.

*Length*.—5.4 cm.

*Diameter*.—2.0 cm at widest point.

*Color*.—Near RHS Yellow-Orange 14C. Flushed Orange-Red N34C at distal end.

Calyx/sepals:

*Quantity per flower*.—5 sepals.

*Shape*.—Deltate.

*Length*.—0.3 cm.

*Width*.—0.2 cm.

*Apex*.—Acute.

*Base*.—Fused.

*Margin*.—Entire.

*Texture*.—Highly pubescent inner and outer surfaces. Color: Inner Surface: Near RHS Green 138B. Outer Surface: Near RHS Green 138B.

Floral bracts:

*Shape*.—Deltate.

*Length*.—1.5 cm.

*Diameter*.—0.7 cm at widest point.

*Color*.—Near RHS Yellow 10B, flushed Greyed-Purple 183B at base, Greyed-Purple 187A at apex, upper and lower surfaces.

*Texture*.—Pubescent.

REPRODUCTIVE ORGANS

Stamens:

*Number*.—5.

*Length*.—8.2 cm.

*Width*.—0.15 cm.

*Color*.—Near RHS Yellow-Orange 14D.

*Anthers*.—Length: Approximately 0.4 cm. Diameter: Approximately 0.2 cm. Shape: Linear. Color: Near RHS Yellow-Orange 14D, small flush near Orange-Red 34C. Pollen: Moderate, colored near Greyed-Orange 163D.

Pistil:

*Number*.—1.

*Length*.—9.1 cm.

*Style*.—Length: 8.5 cm. Color: Near RHS Yellow-Orange 22B.

*Stigma*.—Globular, colored near Yellow-Green 146A.

*Ovary*.—Sericeous texture. Approximately 0.2 cm in diameter. Colored near Green 137A.

OTHER CHARACTERISTICS

Disease and pest resistance: Not observed to be susceptible nor resistant to normal pests of *Rhododendron* hybrid. Increased tolerance to mildew *Erysiphe azalea*.

Temperature tolerance: USDA Zone 6.

Fruit/seed production: Not observed to date.

What is claimed is:

1. A new and distinct cultivar of *Rhododendron* plant named 'QBACKB' as herein illustrated and described.

* * * * *